United States Patent
Daum et al.

[11] Patent Number: 5,813,813
[45] Date of Patent: Sep. 29, 1998

[54] SURGICAL MANIPULATOR

[75] Inventors: Wolfgang Rudolf Daum; Jörg Schmiedeke, both of Schwerin, Germany

[73] Assignee: Daum GmbH, Schwerin, Germany

[21] Appl. No.: 963,084

[22] Filed: Nov. 3, 1997

Related U.S. Application Data

[63] Continuation of Ser. No. 670,005, Jun. 25, 1996, abandoned, which is a continuation of Ser. No. 206,450, Mar. 4, 1994, Pat. No. 5,599,151.

[30] Foreign Application Priority Data

Mar. 4, 1993 [DE] Germany .......................... 43 06 786.7

[51] Int. Cl.⁶ ...................................................... B25J 3/00
[52] U.S. Cl. .................. 414/7; 294/25; 294/111; 623/64; 600/104
[58] Field of Search ......................... 414/2, 7, 8; 294/25, 294/100, 106, 111, 99.1; 623/57, 64; 606/205, 210; 128/897, 749, 751; 600/104

[56] References Cited

U.S. PATENT DOCUMENTS

| | | |
|---|---|---|
| 422,373 | 3/1890 | Caldwell . |
| 2,733,545 | 2/1956 | Guadagna . |
| 2,765,930 | 10/1956 | Greer et al. . |
| 3,133,649 | 5/1964 | Serrell ......................................... 414/2 |
| 3,212,651 | 10/1965 | Specht et al. . |
| 3,266,059 | 8/1966 | Stelle . |
| 4,298,300 | 11/1981 | Francois et al. . |
| 4,302,138 | 11/1981 | Zarudiansky ................................. 414/5 |
| 4,315,650 | 2/1982 | Yoshida . |
| 4,575,297 | 3/1986 | Richter ................................. 414/730 X |
| 4,834,761 | 5/1989 | Walters . |
| 4,853,874 | 8/1989 | Iwamoto et al. ........................ 414/2 X |
| 4,921,293 | 5/1990 | Ruoff et al. . |
| 4,986,723 | 1/1991 | Maeda . |
| 5,025,778 | 6/1991 | Silverstein et al. . |
| 5,092,646 | 3/1992 | Smallridge . |
| 5,395,386 | 3/1995 | Slater .................................. 128/751 X |
| 5,599,151 | 2/1997 | Daum et al. ................................ 414/7 |

FOREIGN PATENT DOCUMENTS

| | | |
|---|---|---|
| 0 640 319 | 3/1995 | European Pat. Off. . |
| 688 538 A1 | 12/1995 | European Pat. Off. . |
| 2 416 094 | 8/1979 | France . |
| 225619 | 8/1985 | German Dem. Rep. . |
| 335838 | 4/1918 | Germany . |
| 20 48 563 | 5/1980 | Germany . |
| 29 39 452 | 2/1983 | Germany . |
| 42 23 792 | 9/1993 | Germany . |
| 43 06 786 | 2/1994 | Germany . |
| 6-54801 | 3/1994 | Japan ..................................... 600/104 |

OTHER PUBLICATIONS

Gliederung von Manipulaturen, Die Technik, 2 Feb 1964, pp. 92–96.

*Primary Examiner*—Donald W. Underwood
*Attorney, Agent, or Firm*—Merchant, Gould, Smith, Edell, Welter & Schmidt, P.A.

[57] ABSTRACT

The present invention relates to a surgical manipulator for remotely grasping and manipulating things in response to movements of a human hand controlling the device. Movements of human fingers can be transmitted to mechanical finger-like devices through mechanical cables and linkages. In one embodiment the linkages include a mechanical movement reduction device to translate large hand movements to smaller distal movements. Various structures are provided at the proximal and distal ends for sensing and replicating the movements of a human hand.

10 Claims, 10 Drawing Sheets

SURGICAL MANIPULATOR

This is a Continuation of application Ser. No. 08/670,005, filed Jun. 25, 1996 and now abandoned; application Ser. No. 08/670,005, which is a continuation of application Ser. No. 08/206,450, filed Mar. 4, 1994, now U.S. Pat. No. 5,599,151.

TECHNICAL FIELD OF THE INVENTION

The invention relates a mechanical manipulator for working in inaccessible areas and cavities.

BACKGROUND OF THE INVENTION

In the recent field of endoscopic minimal invasive surgery and also in many technical sectors, it is frequently difficult to work with manual dexterity in inaccessible areas. For that reason many appliances have been developed to execute special gripping and manipulating work. The disadvantage of those special tools is however that the appliances must repeatedly be exchanged as the operation proceeds. It would thus be an advantage if the operator could work with a miniature artificial hand in inaccessible areas.

The invention deals with the problem of providing the operator with a manipulator which directly takes up the movements of the human arm, hand and fingers and transmits these movements directly to an identical unit in terms of form and function, which can be pushed through narrow channels, such as the trocars of modern minimal invasive surgery into the site of operation, where it functions in the same way as a hand and is simultaneously simply constructed so that it is easy to wear.

Appliances which take up the movement of human movements of the remote control of gripping devices in robots are already known. U.S. Pat. No. 4,302,138 and French Patent No. 2,416,094 show an appliance which measures the movement of the human hand either directly by electric sensors situated in the hand or via mechanical rods to electric sensors further away from the hand. These sensors pass on the electric signal to control a gripping device.

Appliances which function like a human hand in terms of form and function are already known. None, however, are controlled directly by the human limbs in a purely mechanical fashion. In that respect U.S. Pat. No. 4,834,761 shows an appliance which is operated by means of a system of hydraulically acting pistons and the movement of which is transmitted to the fingers by means of cords (strings) using pulley constructions. U.S. Pat. No. 5,092,646 shows an appliance powered by servo-motors in which a whole finger of one hand is bent via a double winch construction and stretched via a spiral spring using stretch cords. In U.S. Pat. No. 4,986,723 the stretch movement is also executed with the aid of a spiral spring and the bending movement with the aid of a pulley. U.S. Pat. No. 4,921,293 also shows fingers moved by means of pulley constructions.

In the aforesaid appliances, the control signals from the control unit are transmitted to the gripping device electrically. Mechanical transmission is known in DE-AS-2048563, in which a firmly installed working arm is moved via pulleys. The movement executed by the appliance arm, however, is not taken up and transmitted from the arm of the operator, but by a control arm which has to be moved by that person. In the case of that appliance, the operator must continually consider how to steer the control arm in order to bring the working arm into the position required.

The same occurs in the idea presented in DE-2939452, which also concerns not a portable but a fixed appliance. Both arms have a direct swivel connection via an axle so that swivelling the control arm leads to a corresponding swivel movement of the secondary arm. Because of that design, however, the appliance cannot be used to control movements through a narrow channel such as that of a trocar. That, however, is the aim of one of the features of the invention described here. The two parallelograms shown in specification DE-2939452 are integral components of the arms without which no movement whatsoever can be executed. Movement transmission is achieved by pushing or pulling wires or threads. The levers or pantographic elements serve only to correct the path of these wires or threads and are not integral parts of the appliance sections. Movement of the appliance sections is also possible without the above elements, so that they are used only to adjust the Bowden cable movement. That adjustment is important, e.g., if a new and smaller distal hand is to be attached to an existing proximal one. Special movements can thereby be attained in the manner specified below.

All these prior appliances are unsuitable for use in inaccessible areas with small dimensions—such as the human abdominal cavity—owing to their size and complicated structure.

BRIEF DESCRIPTION OF THE DRAWINGS

The following figures elucidate the invention submitted in this application:

FIG. 6B 1–4 are schematic views of generation and movement sequence of a nonlinear transmission and FIG. 6C is a schematic view of an example of a special application of an unnatural position to the human hand;

FIGS. 7A&B are schematic views of joints of a particularly small distal appliance extremity in different positions;

DETAILED DESCRIPTION OF THE PREFERRED EMBODIMENTS

Figure 1:
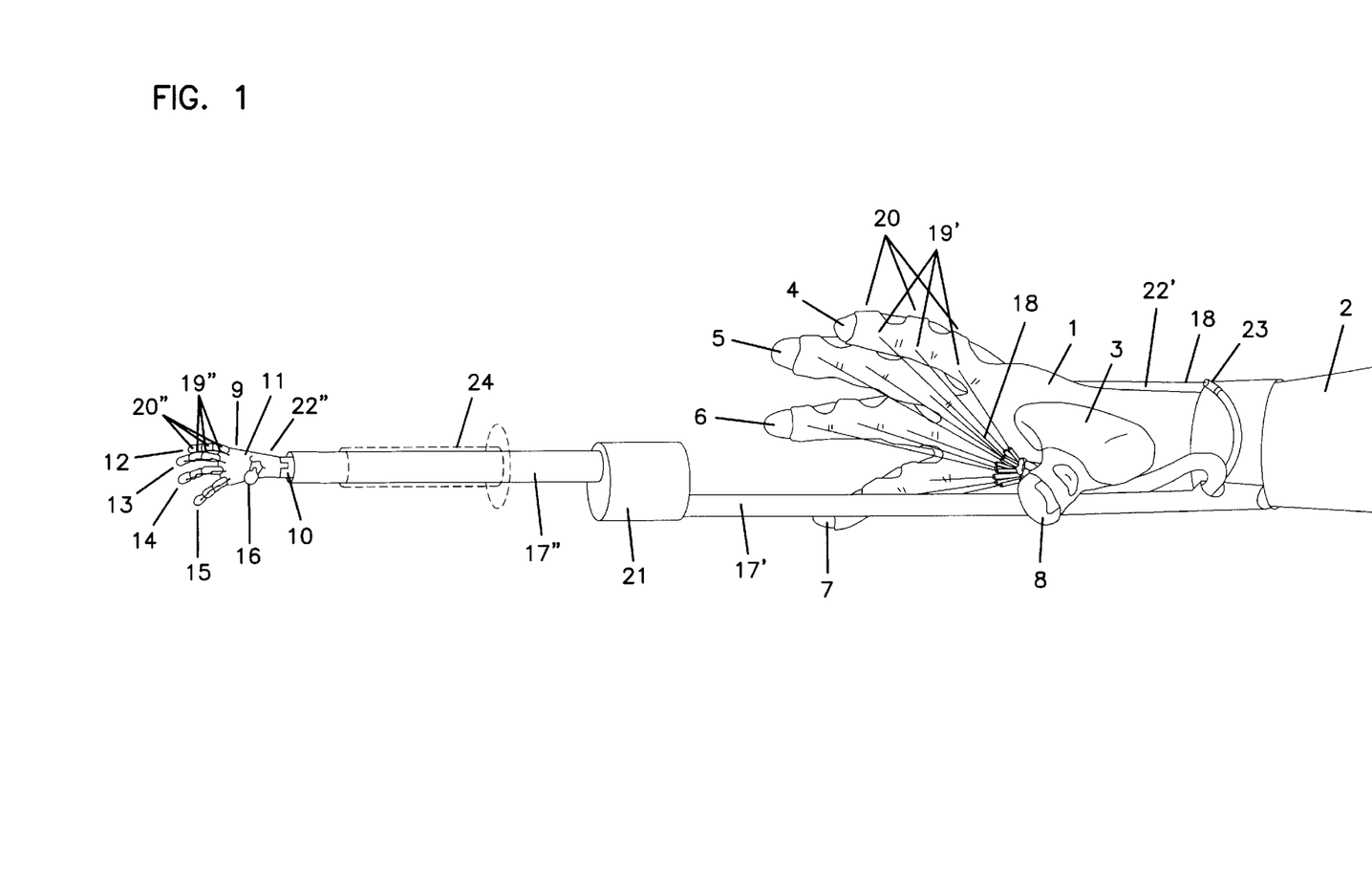
FIG. 1 is a perspective view of the appliance.

FIG. 1 shows a total view of one preferred form of the appliance. It comprises the holder 1 for the human extremity lower arm 2, trunk of the hand 3 and the five fingers 4, 5, 6, 7 and 8 with individual sections. Holder 1 here may take the form of a type of rubber glove, the fit of which corresponds exactly to the human extremity and which follows the movement of the human extremity easily and without hindering the extremity. The appliance further comprises the distally situated extremity 9 which is made up of corresponding sections, viz. lower arm 10, trunk of the hand 11 and the five fingers 12, 13, 14, 15 and 16. The form and function thereof corresponds to the human extremity. A rigid conduit 17 ' and 17" houses the wires 18, the proximal ends of which 19' are flexibly connected to sections 20 of the rubberlike holder 1 and the distal ends of which 19" are flexibly connected to the sections 20" of the distal extremity. A coupling section 21 described further below adjusts the direction and distance of the wires 18 moved by the human hand to the requirements of the distal extremity.

As the joints of the proximal extremity are connected to each other directly and mechanically by means of a coupling section, it is possible to move a distal section by moving the corresponding section of the human extremity. In FIG. 1, for example, if trunk of the hand 3 is bent upwards against lower arm 2 towards the back of the hand, then wire 22' is pushed into its sheath 23—Bowden cable. In coupling section 21 this movement is adjusted to the circumstances of the distal hand so that the distal end 22" pulls the trunk of the distal hand 11 and thus bends it against the distal lower arm 10.

This movement mechanism enables the distal hand to be folded up to such an extent that it can be pushed by the front part of conduit 17" through a trocar 24 to or into the operation site.

The movement of the upper arm against the lower arm is not shown in this example. The Bowden cables may have different dimensions. It can thus be advisable to use thicker cables for transmitting the movement of larger human limbs and thinner cables to transmit those of smaller limbs. Different materials such as metals or synthetics can also be used. For instance, it may be advisable to use synthetics such as polytetrafluoroethylene (Teflon®) or materials with similarly low coefficients of friction to optimize the sliding properties of the cables inside the sheaths.

Figures 2, 2A, 2B:
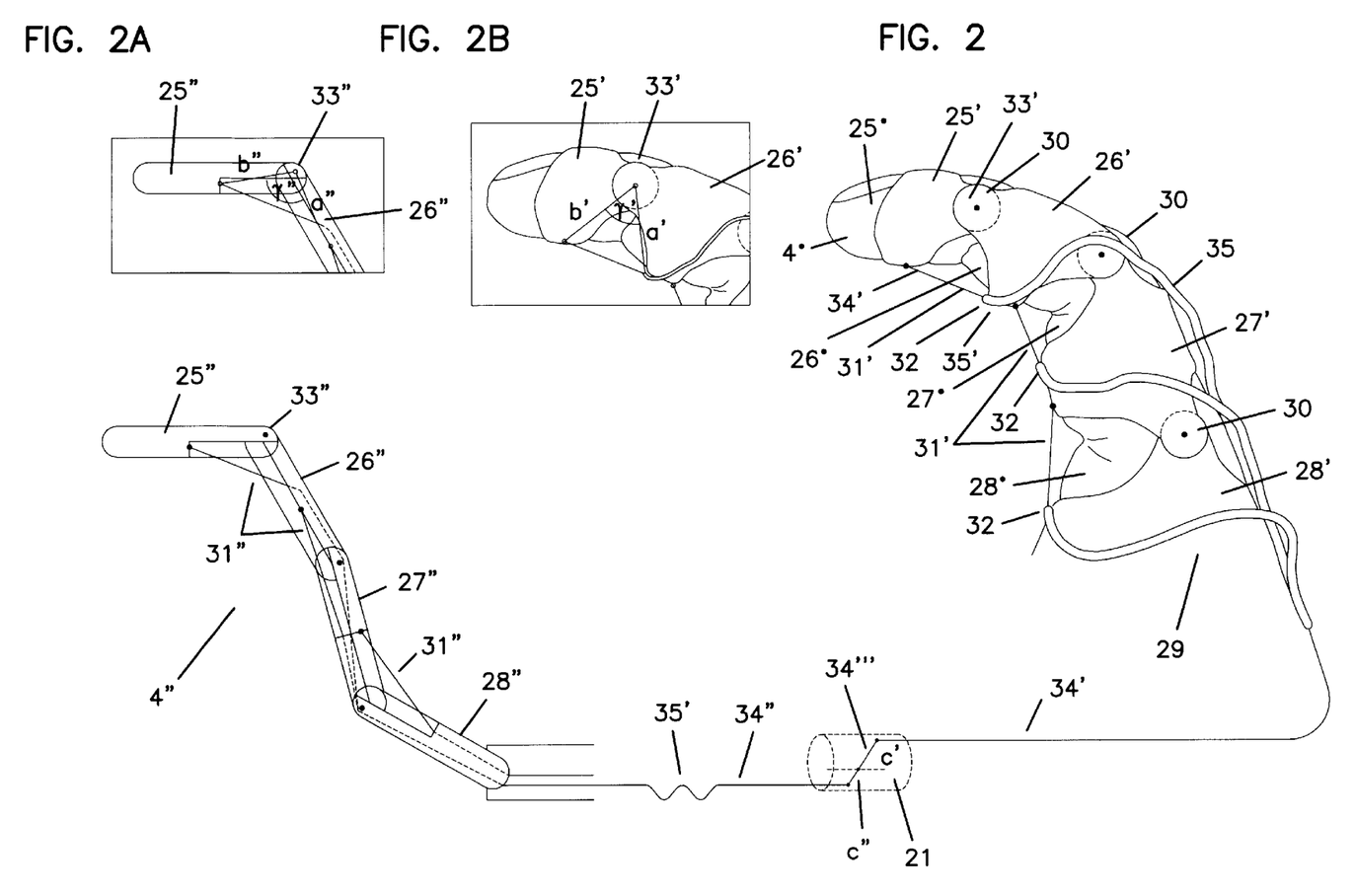
FIG. 2 is a schematic view of the appliance transmission.
FIG. 2A is a detailed schematic view of a distal finger.
FIG. 2B is a detailed schematic view of a finger in FIG. 2.

FIGS. 2A–2B elucidate the transmission mechanism more clearly. It shows a human finger 4° with the end section 25°, middle section 26°, base 27° and the corresponding middle section of the hand 28°. The finger fits into the holder 29, which in this case does not take the form of a rubber glove, and which comprises the corresponding sections 25', 26', 27' and 28' and of joints 30. At the distal end, there is the appliance finger 4", enlarged in the figure for better representation, with the corresponding sections 25", 26", 27" and 28". Contrary to the transmission of movement in FIG. 1, in this case the proximal ends 31' of the wires do not run exposed across the hollow hand, but directly into the sheath 32 attached to the neighboring section with which they form a type of Bowden cable. Distal parts 31" of the wires on the distal finger are located partly in the finger sections. Again contrary to FIG. 1, the conduit is not rigid, as indicated by the curving path 35" of the wire in the distal part. Only one wire is shown to give a clearer representation.

If the operator bends the end section of his finger 25° against the middle section 26°, the corresponding sections 25' and 26' also bend around their common joint 33', as the holder follows the movement of the finger without hindrance. As a result, proximal transmission wire 34' is pushed into a Bowden cable sheath 35'. In coupling section 21, the direction in which the wire moves is reversed by a lever 34'". This allows the finger end section 25" of the distal finger to be bent against finger middle section 26" around the common joint 33".

The path covered by proximal part 34' of the wire can be determined by the cosine formula with the values shown in FIG. 2B. These are calculated from distance b' from the wire attachment to the pivot 33', distance a' from the sheath opening attached to the neighboring finger section to the pivot and the angle of movement γ'. Corresponding values a", b", and γ" are shown in FIG. 2A for the distal side. The distances a", b", a' and b' as well as coupling rods c" and c' can be used to adapt the angle transmission ratio γ"/γ', which will normally be equal to 1 for most applications.

Figure 3:
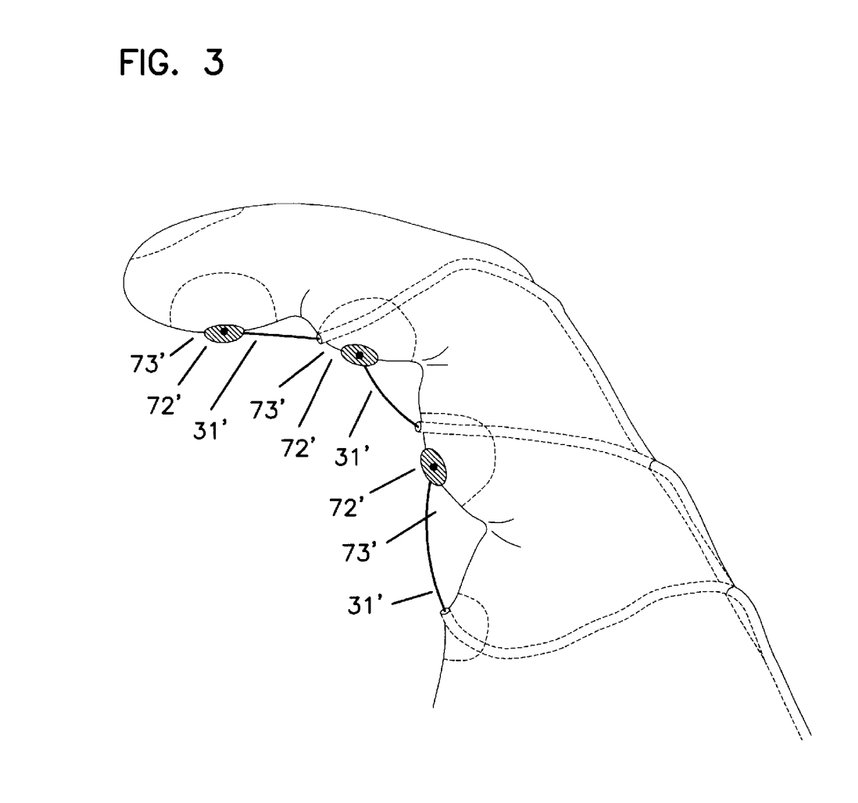
FIG. 3 is a view of a finger holder and glove with integrated Bowden cables.

To illustrate the angle ratios, FIG. 2 shows a holder with joints and therefore clear pivot axes. The preferred design shown in FIG. 3, however, shows a glove, represented by only one finger, in which the Bowden cables are integrated in the rubber material. Wires 31' are then movable, e.g., at axes 72' or with ball joints which are not shown here attached to joint fixtures 73' which are permanently integrated in the glove. The advantage of this type of fixture is the exact fit for the human extremity and the ease of movement.

It must be pointed out that owing to the smallness of the distal finger, it can be constructed with easily produced parts. Further, Bowden cables can be used to open out the fingers laterally.

Figure 4:
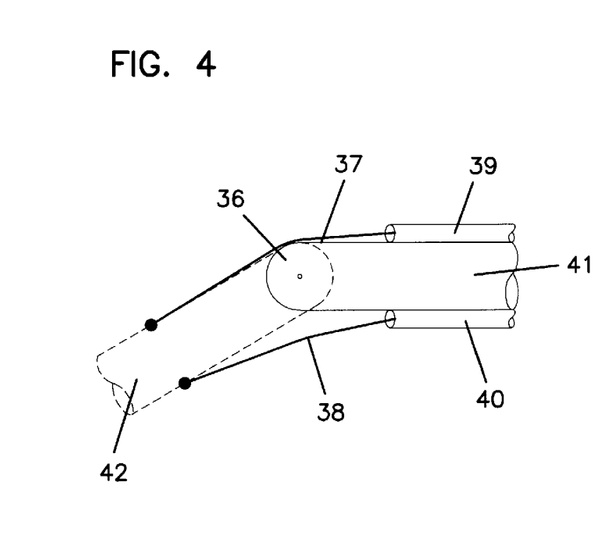
FIG. 4 is a schematic view of the attachment of two threads to a distal finger.

By means of joint 36 of a distal finger, FIG. 4 shows that it is also possible to use two threads 37 and 38 instead of the wires. Sheaths 39 and 40 corresponding to the threads are located above and below a finger section 41. By loosening thread 37 and tightening thread 38, finger section 42 is bent around joint 36 and vice versa. Corresponding parts to transmit pulling movements on the threads can be located on the corresponding proximal sections of the appliance.

Figure 5:
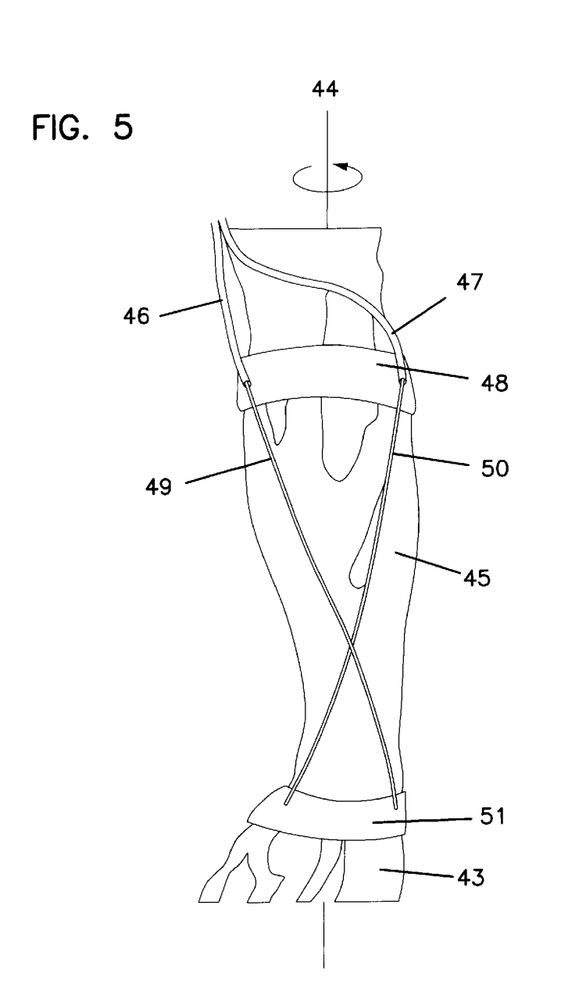
FIG. 5 is a schematic view (with environment) showing a Bowden cable attachment for taking up the rotary movement of the hand around the longitudinal axis of the lower arm.

FIG. 5 shows how the rotary movement of human hand 43 around axis 44 of the lower arm 45 is taken up by means of two Bowden cables. In that case, sheaths 46 and 47 end at arm part 48 of the holder and cables 49 and 50 which cross on lower arm 45 end at the hand part of the holder. If hand 43, seen from lower arm 45, is now turned counterclockwise in the direction of the arrow, then cable 50 is pushed into its sheath 47 and the other cable 49 pulled out from its sheath 46. Corresponding distal rotary movement can be achieved by wires crossing in the opposing direction between the lower arm and hand of the appliance.

Figure 6A:
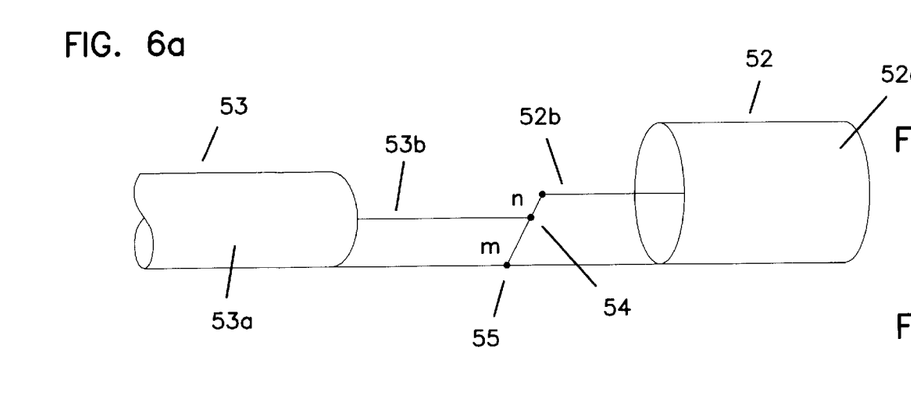
FIG. 6A is a schematic view of the concept for reduction of the human hand movement by means of a pantographic appliance.
Figure 6B:
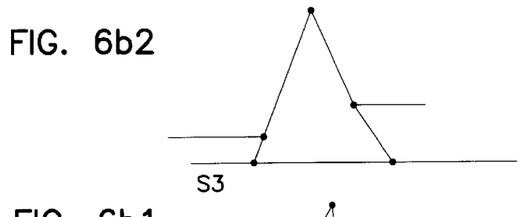
Figure 6B:
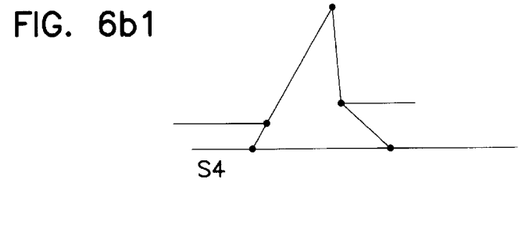
Figures 6B, 6B:
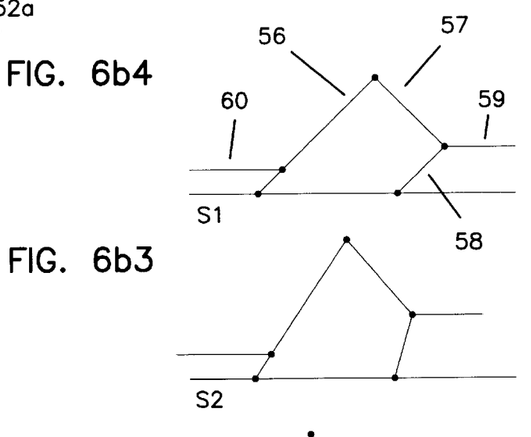
Figure 6C:
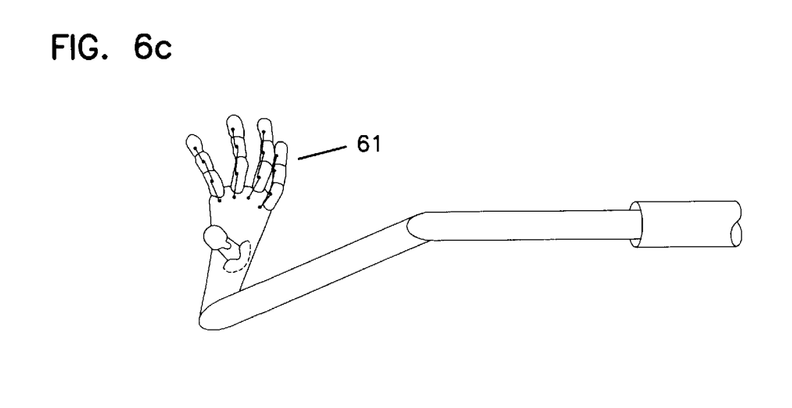

FIGS. 6a–c are intended to elucidate the idea of transmitting the different proportions of the human hand of the operator to those of the appliance. The problem may result on the one hand in that the appliance hands may have different dimensions. On the other hand, the problem may arise from the wish to achieve different effects from special hand movements. An example of this would be excess tilting of the finger end section against the finger middle section with an angle transmission ratio of, e.g., $\gamma''/\gamma'=2$, while the other joints should retain a true-to-angle ratio of $\gamma'''/\gamma'=1$. The solution to this problem as described in claim 2 utilizes the laws of leverage and rod constructions in the manner of a pantograph.

Adjusting the distances covered has already been explained by means of lever 34''' in FIG. 2. FIG. 6A shows a different construction of this. Two Bowden cables 52 and 53 are attached with their sheaths 52a and 53a. Wires 52b and 53b can be rotated and—contrary to lever 34''' in FIG. 2—are attached to the coupler 54 on the same side of pivot 55 so that no change of direction occurs here. If wire 52b is now pushed out of its sheath 52a, wire 53b is then pushed into its sheath 53a. The ratio of the path difference of wire 52b to wire 53b results, e.g., from the theorem of rays based on the variably adjustable rod connections n and m.

FIG. 6b-1–4 give clearer illustrations of the function of the pantographic mechanism. This involves a transmission element with three coupling rods 56, 57 and 58 and non-constant angle transmission ($\gamma'''/\gamma'$=constant, cf. FIGS. 2A and 2B. This is illustrated by example of four movement stages s1, s2, s3 and s4 of the movement. During stages 1 and 2, constantly pushing the wire 59 forwards also pushes wire 60 forwards. As from stage s3, however, the direction in which wire 60 moves is reversed, although wire 59 is still constantly pushed forwards, stage 4. It is thus possible for special operations to obtain specific movement sequences which could not be achieved by the human hand. FIG. 6c, for example, shows how appliance hand 61 can be bent at an unnatural angle for the human hand.

By means of such transmission elements and by the selection of distances a' and b' of the proximal sections and a'' and b'' of the distal sections as shown in FIG. 2 it is possible to convert a versatile manipulator into an instrument for special applications.

In medical technology, appliances must normally be constructed so that they can be sterilized. Materials may not be able to withstand the temperatures or humidity occurring in the steam sterilizers (autoclaves) used for that purpose or the appliances have to be dismantled to ensure that all concealed cavities can be cleaned and subsequently sterilized. This problem can be avoided for the appliance hand shown here by covering the hand, similar to the human surgeon's hand, with a rubber elastic glove. The glove can be discarded after the operation, the appliance hand itself need only be disinfected.

Figures 7A, 7B:
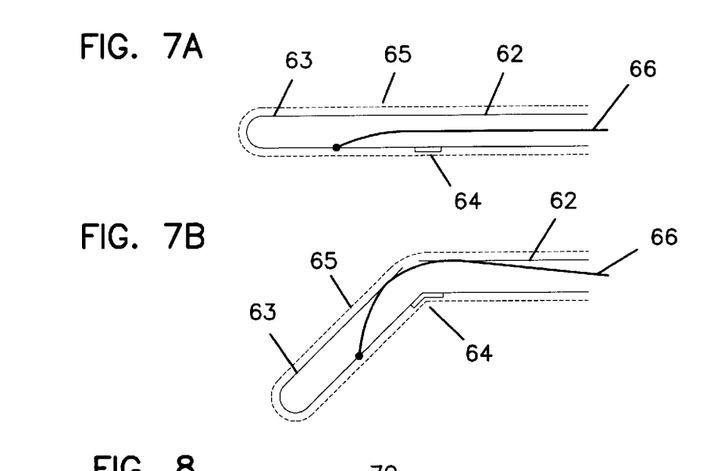

For extremely small distal extremities, a rubber elastic coating can also act as a joint. This is illustrated by two sections 62 and 63 in FIG. 7a and 7b. These sections are connected to a slightly thicker piece of rubber 64 which is adhered to the lower sides of the finger sections. The aforesaid rubber elastic coating 65 surrounds both sections 62 and 63 and others. When pushing out wire 66, section 63 avoids the pressure generated by bending against section 62 holding onto the adhered piece of rubber 65, FIG. 7b. The rubber coating, which is now tensed, can return to its original position by relaxing section 63, FIG. 7a.

Figure 8:
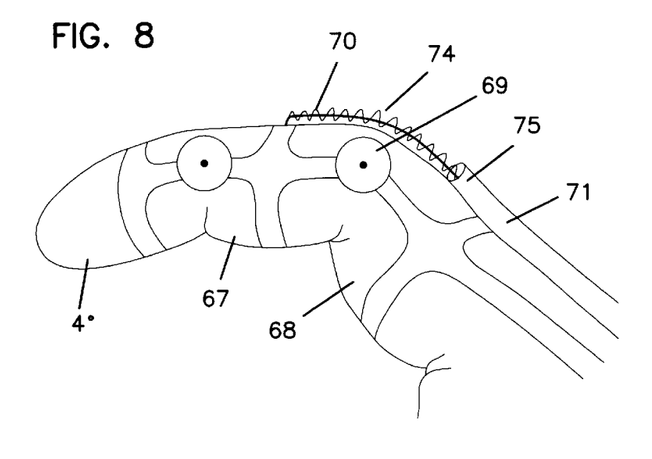
FIG. 8 is a view of an alternative preferred embodiment showing the attachment of the Bowden cables to the top side of the finger.

In the case of exposed wires 18, 49 and 50 shown in FIGS. 1 and 5, it is possible for the wires to veer off to the side, leading to an error in transmission. FIG. 8 shows a human finger 4° in which movement of the middle section 67 against base section 68 is executed by means of a joint 69 and a Bowden cable 71 lying on the finger. The exposed section of wire 70 is coated with a spiral spring 74 which safely guides the wire into its sheath 75 without shearing.

Figures 9, 10:
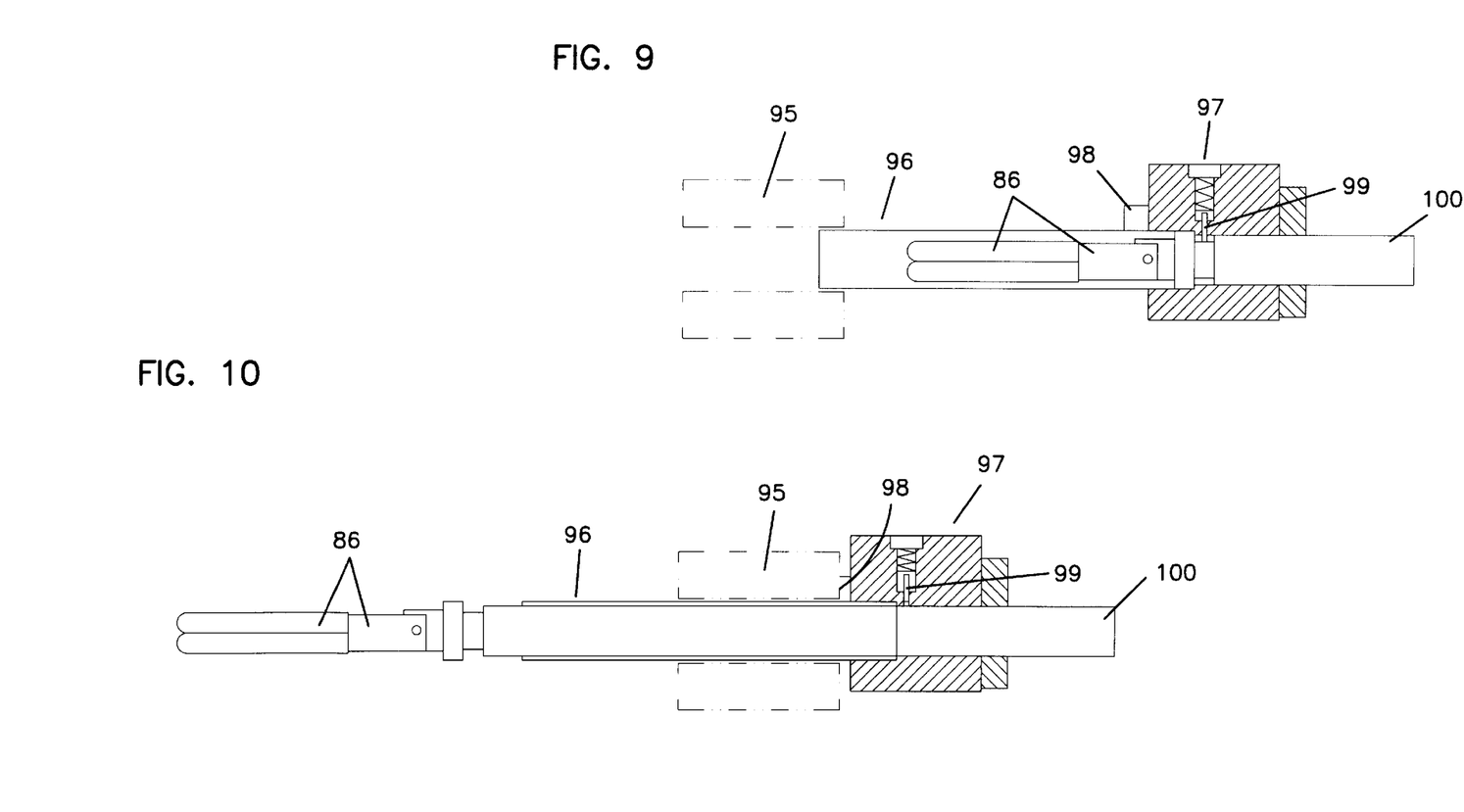
FIG. 9 is a schematic view of a distal hand in a protector sleeve.
FIG. 10 is a schematic view of a distal hand extending out of a protector sleeve.

FIGS. 9 and 10 show a construction for protecting the distal hand 86. FIG. 9 shows the distal hand 86 inside the protection tube 96. This will be so if the manipulator is pushed through the trocar shell 95 into the human body. When pushed into the trocar's 95 shell the button 98 will contact the trocar's shell 95, FIG. 10. This results in release stopping pin 99 which is normally held in position by a spring 97. The distal hand is then released and may be moved inside the human body. This mechanism also works in reverse.

Another advantage is the possibility of rotating the transfer pipe 100 so that the distal hand 86 is turning to all desired directions.

Figure 11:
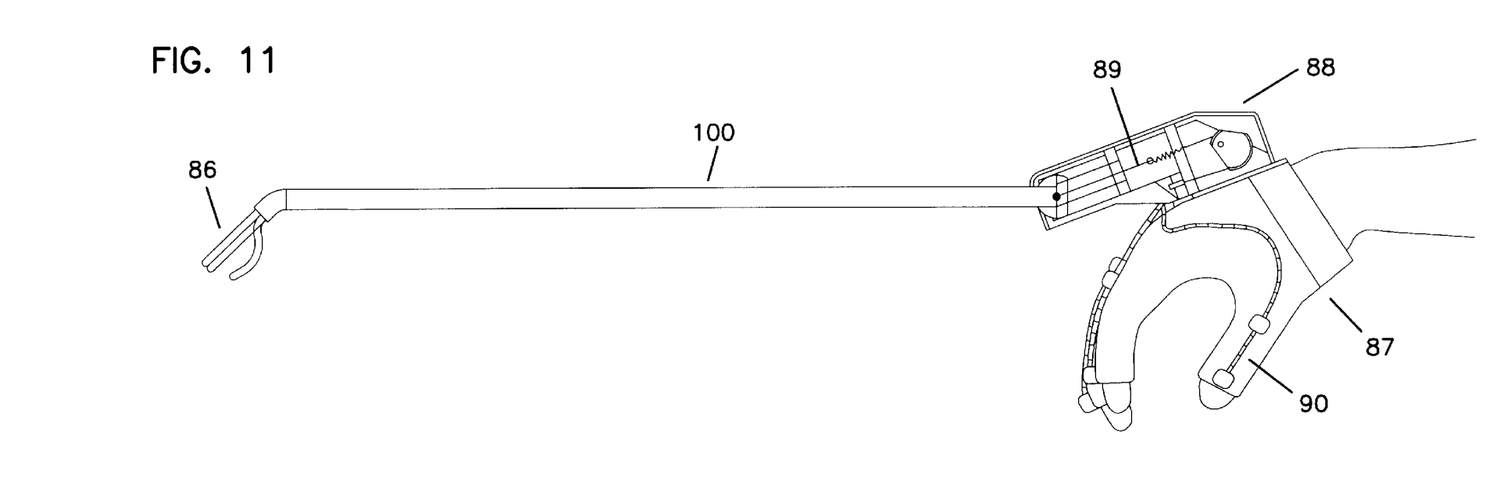
FIG. 11 is a side view with positions broken away of an alternate preferred embodiment of the appliance.
Figure 12:
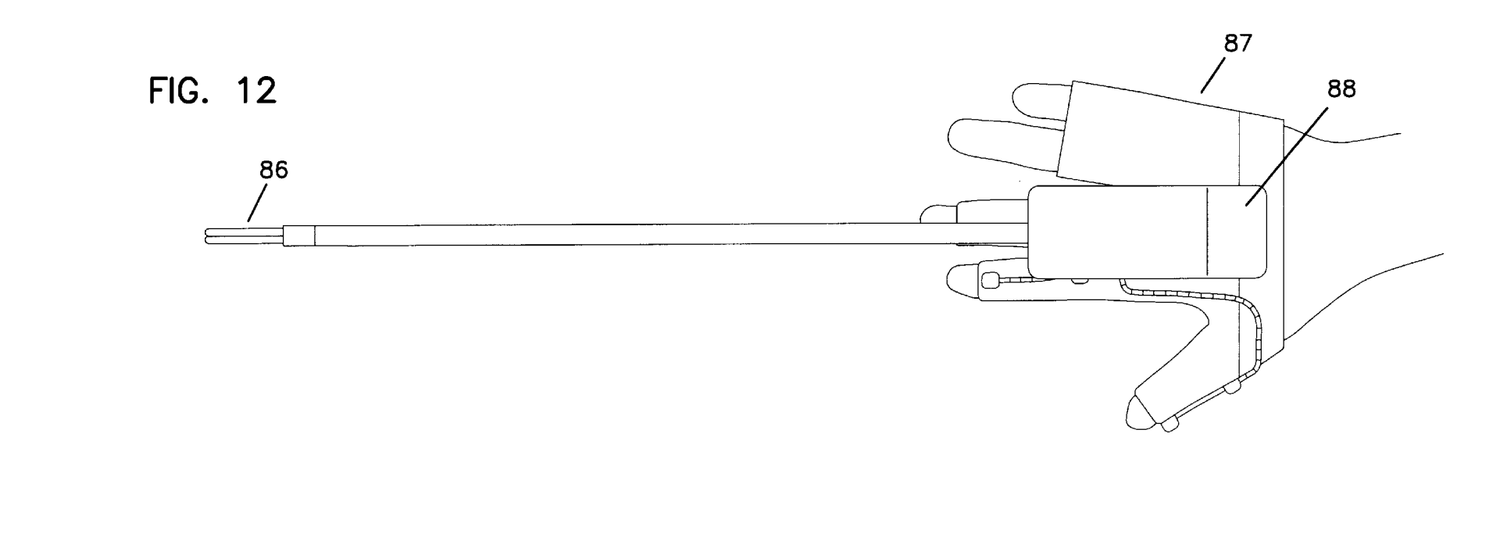
FIG. 12 is a top plan view of the embodiment in FIG. 11.
Figure 13:
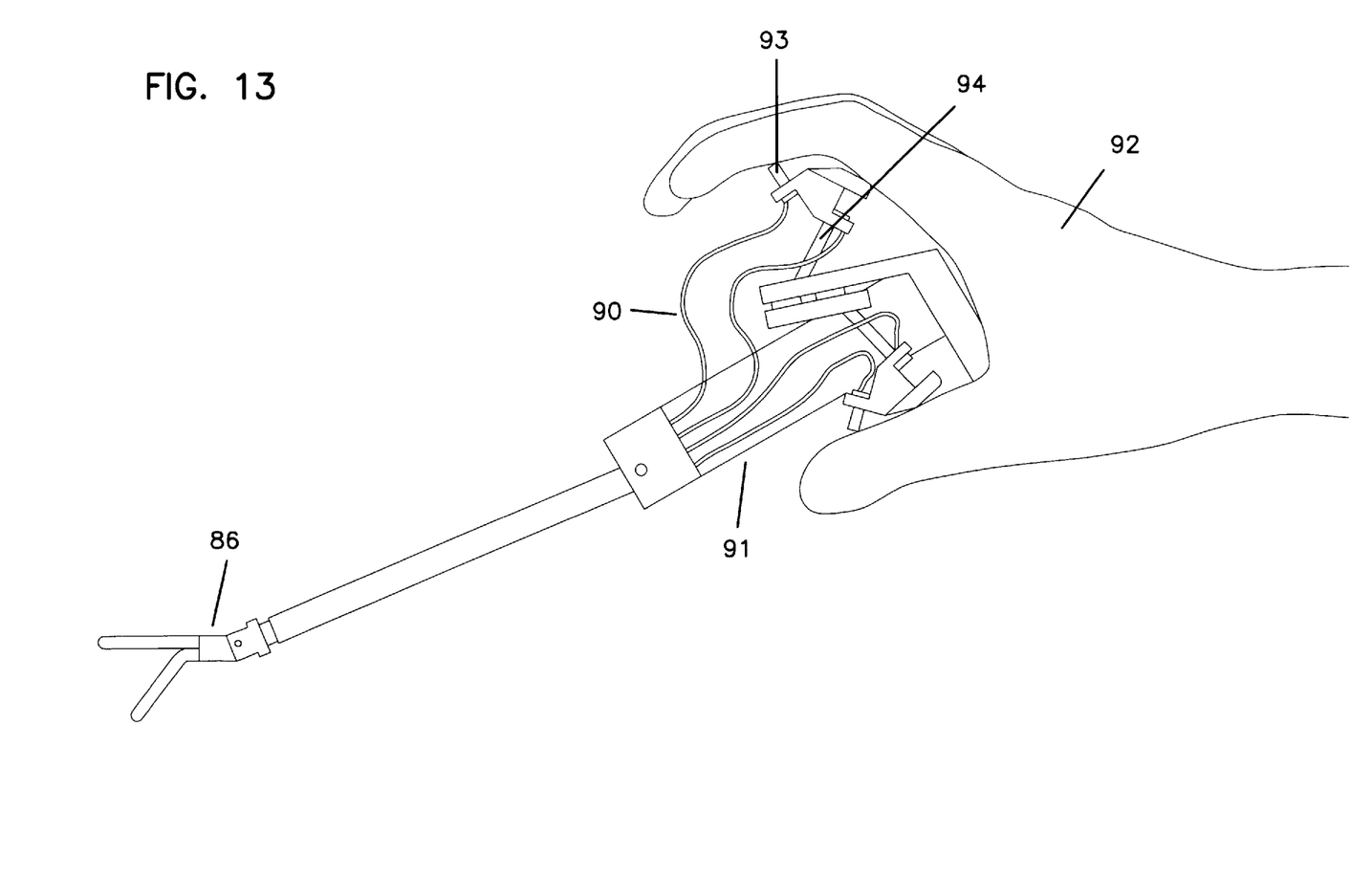
FIG. 13 is a schematic side view with portions broken away of a further preferred embodiment of the appliance.

FIGS. 11, 12 and 13 are alternate preferred embodiments showing different locations of the coupling section 88 and 91. Because the back side of the human hand is plain and almost never bending, it builds an easy location to put the coupling section. In FIGS. 11 and 12 the Bowden cables 90 are located on top of the proximal part of the manipulator. They also may be inserted in the elastic material of the proximal glove 87. Inside the coupling section 88 Bowden cables 89 move without their outer shell. Bowden cables move inside the transfer pipe 100 to the distal hand 86.

FIG. 13 shows a surgical manipulator with proximal part 91 at the inside of the human hand 92. Because the rod assembly 93 and 94 of this kind of manipulator with Bowden cables 90 can be built in a more solid way the instrument can withstand more strength from the human hand. The advantage is a manipulator which can grasp in a stronger way. With the manipulator of FIG. 12 the surgeon is in opposite to the manipulator of FIG. 13 able to palpate.

As a further refinement on this invention, it is possible to employ a distal finger design for maximum manipulability and ease of cleaning. FIGS. 14–18 disclose another preferred embodiment thereof.

Figure 14:
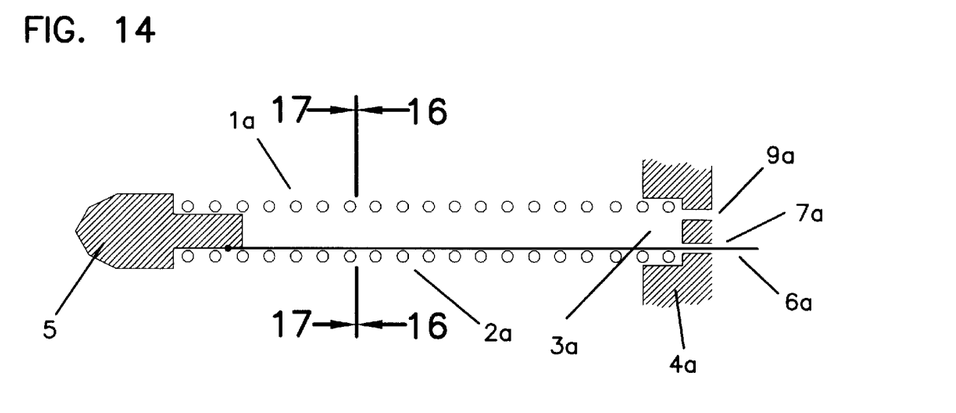
FIG. 14 is a schematic view of an alternate preferred embodiment of a distal finger.
Figure 15:
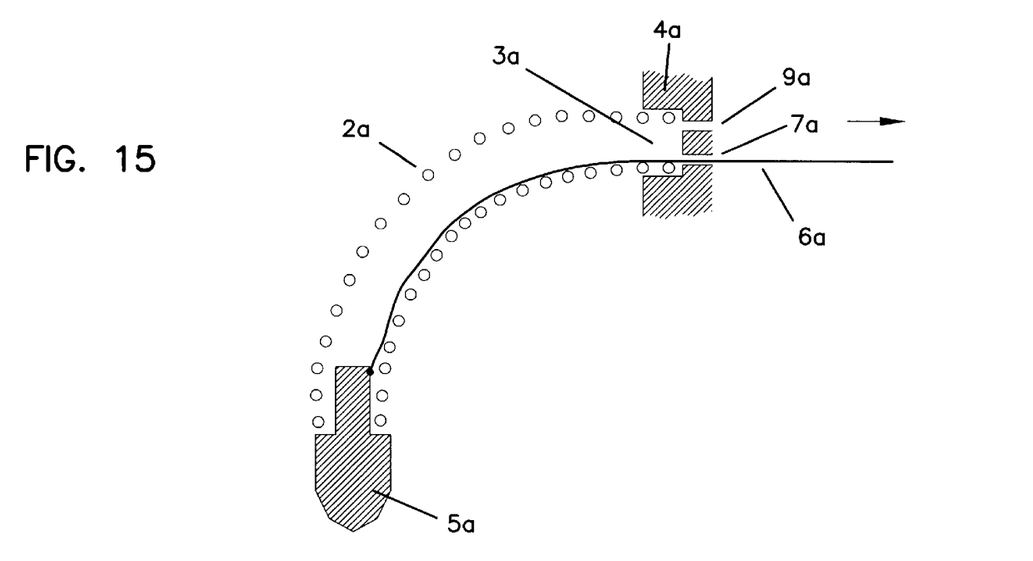
FIG. 15 is a view like FIG. 14 with the finger actuated.

The principle of this new type of appliance is demonstrated in the cross section of a finger 1a shown in FIG. 14. The finger 1a comprises a spiral spring 2a inserted in a drill hole 3a on the base of the hand 4a. The spiral spring 2a is connected to the end of the finger with a metal bolt 5a. A cable 6a is firmly attached to the metal bolt 5a and runs inside and along the spring 2a through a drill hole 7a of hand section 4a. In FIG. 14 the cable is slack, while in FIG. 15 it is pulled from the proximal end, see arrow. As a result of the tension, the spiral spring is bent and the finger also bends.

Figure 16:
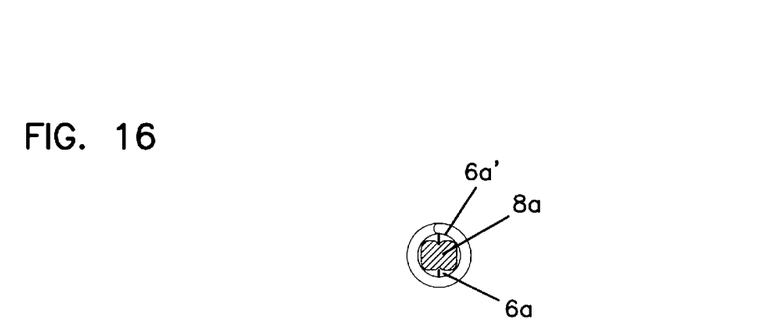
FIG. 16 is a cross-sectional view taken along line A—A of FIG. 14.

In order to improve guidance of the cable 6a, the spiral spring 2 may contain a rubber section 8, as shown in FIG. 16. Other cables e.g. 6a' may be inserted via other drill holes 9a, FIGS. 1a and b, to extend the bending potential of the finger. Cable 6a pulls the finger down while 6a' pulls up.

Figure 17:
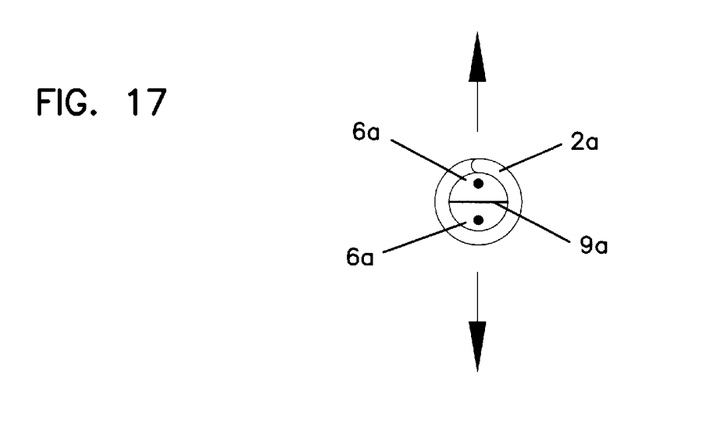
FIG. 17 is a view like FIG. 16 except taken along line B—B of FIG. 14.

FIG. 17 shows a cross section of a finger which is given stability and a priority direction of bending by means of a thin metal sheet 9a inserted in the spiral spring 2a. The priority direction of bending is indicated by the arrows.

Figure 18:
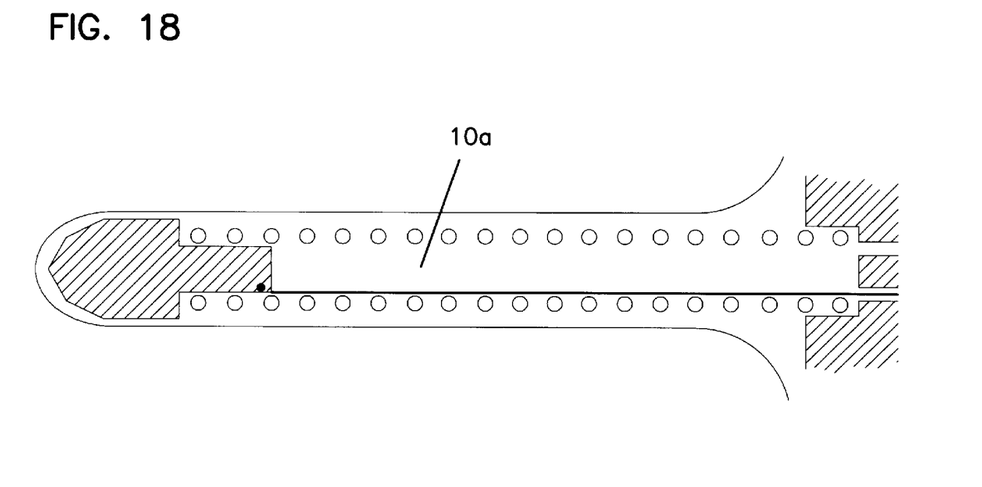
FIG. 18 is a view like FIG. 14 except being covered (in section) by a rubber sheath.

FIG. 18 shows encapsulation in rubber 10a to improve the cleaning or sterilization properties. This prevents the occurrence of any cavities or spaces which are difficult to clean. This design replaces the inner section 8 and means that the finger with spiral cannot catch on any other parts during work with the manipulator. In addition, the distal hand can thus be given an appearance similar to that of the human hand. That suggestion gives the operator a familiar relation to his environment which is important for the success of his work.

To prevent damage to the distal fingers 86 when the manipulator is inserted into a medical trocar 95, the fingers may be inserted through a device shown in FIGS. 9 and 10. This device protects the fingers 86 within tube 96 when inserted into trocar 95. Depressing button 98 releases pin 99 so that the fingers can be thrust forward into the position shown in FIG. 10. After the operation is completed, distal fingers 86 can be withdrawn back into tube 96 and maintained in place by pin 99 of spring block 97. Notice in this case that trocar 95 automatically actuates element 98 when it comes into contact with release button 98.

We claim:

1. A mechanical hand manipulator for use in surgery, comprising:
   (a) a proximal part having a holder for receiving a human hand including a plurality of human digits;
   (b) a distal part having a plurality of independently moveable distal digits, each of said digits having at least one articulation and, wherein said distal part is of a size sufficiently small to pass through a trocar to a surgical site; and
   (c) a mechanical coupling portion mounted to said holder at a dorsal aspect of said human hand and connected between said proximal and distal parts to transfer movement between said proximal and distal parts,
   said mechanical coupling portion including a moveable interconnection link and a motion reducer.

2. A mechanical hand manipulator according to claim 1 wherein said moveable interconnection link comprises a cable.

3. A mechanical hand manipulator according to claim 1 wherein said independently moveable distal digits are coated with an elastomeric coating.

4. A mechanical hand manipulator according to claim 1 further comprising a mechanical protection and retraction device for releasably enclosing said plurality of independently moveable distal digits inside said mechanical protection and retraction device, said device including:
   (a) a protection tube having an inside diameter and an outside diameter, said inside diameter of said protection tube being of sufficient size to enclose said plurality of independently moveable distal digits and said outside diameter being of sufficient size to permit said protection tube to slide within a trocar shell, and
   (b) a release stopping pin to releasably hold said plurality of independently moveable distal digits inside said protection tube, said release stopping pin having a first position and a second position, wherein said plurality of independently movable distal digits is inside said protection tube when said release stopping pin is in said first position and at least one of said plurality of independently movable distal digits is outside said protection tube when said release stopping pin is in said second position.

5. A mechanical hand manipulator according to claim 1 wherein said holder is a glove for receiving at least a portion of a human hand.

6. A mechanical hand manipulator for use in surgery, comprising:
   (a) a proximal part having a glove for receiving a human hand including a plurality of human digits;
   (b) a distal part having a plurality of independently moveable distal digits, each of said distal digits having at least one articulation;
   (c) a coupling portion including a movable, mechanical interconnection link and a mechanical motion reducer connected between said proximal and distal parts to transfer movement of a human digit to a respective distal digit; and
   wherein said motion reducer is mounted on a dorsal portion of said glove.

7. A mechanical hand manipulator according to claim 6 wherein said moveable interconnection link is a cable.

8. A mechanical hand manipulator for use with a user's hand, comprising:
   a glove part, fittable on a thumb and at least one other digit of the user's hand;
   mechanical motion detectors positioned on the glove part to detect movements of the thumb and at least one other digit;
   a mechanical coupler positioned on a dorsal portion of the glove part;
   a mechanical reducer within the coupler coupled to the mechanical motion detectors;
   a shaft extending from the mechanical reducer to a distal end; and
   mechanical digits located at the distal end of the shaft and coupled to the mechanical reducer;
   wherein motion of the mechanical digits is controllable in response to detected movements of the thumb and at least one other digit.

9. A mechanical hand manipulator according to claim 8, further comprising Bowden cables forming couplings between the motion detectors and the mechanical reducer, and Bowden cables forming couplings between the mechanical reducer and the mechanical digits.

10. A mechanical hand manipulator according to claim 8, further comprising a mechanical protector at the distal end of the shaft, the protector including a tube having an inside diameter and an outside diameter, the inside diameter of the tube sufficiently large to enclose the mechanical digits, and a release stopping pin to releasably hold the mechanical digits inside the tube, the release stopping pin having a first position and a second position, the mechanical digits being inside the tube when the release stopping pin is in the first position and at least one the digits being outside the tube when the release stopping pin is in the second position.

* * * * *